US012064143B2

(12) United States Patent
Miller

(10) Patent No.: US 12,064,143 B2
(45) Date of Patent: Aug. 20, 2024

(54) SPINAL CORRECTION SYSTEM AND METHOD

(71) Applicant: Warsaw Orthopedic, Inc., Warsaw, IN (US)

(72) Inventor: Keith E. Miller, Germantown, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 17/975,725

(22) Filed: Oct. 28, 2022

(65) Prior Publication Data

US 2024/0138880 A1 May 2, 2024

(51) Int. Cl.
*A61B 17/70* (2006.01)
*A61B 17/00* (2006.01)

(52) U.S. Cl.
CPC ...... *A61B 17/7019* (2013.01); *A61B 17/7011* (2013.01); *A61B 2017/00407* (2013.01)

(58) Field of Classification Search
CPC ........................................ A61B 17/7002–7031
See application file for complete search history.

(56) References Cited

U.S. PATENT DOCUMENTS

| 7,955,357 | B2 | 6/2011 | Kiester | |
|---|---|---|---|---|
| 8,403,958 | B2* | 3/2013 | Schwab | A61B 17/8605 606/246 |
| 8,425,608 | B2* | 4/2013 | Dewey | A61F 2/44 623/17.16 |
| 9,427,261 | B2 | 8/2016 | Kawakami et al. | |
| 9,833,262 | B2 | 12/2017 | Lim et al. | |
| 9,872,709 | B2 | 1/2018 | Luhmann | |
| 10,363,069 | B2 | 6/2019 | Simpson et al. | |
| 10,617,446 | B2 | 4/2020 | Lynch et al. | |
| 10,952,776 | B2* | 3/2021 | Sharifi-Mehr | A61B 17/7002 |
| 11,071,568 | B2* | 7/2021 | Charest | A61B 17/7017 |
| 11,304,729 | B2 | 4/2022 | Pool | |
| 11,446,064 | B2* | 9/2022 | Sharifi-Mehr | A61B 17/663 |
| 2009/0187248 | A1 | 7/2009 | Dewey et al. | |

(Continued)

FOREIGN PATENT DOCUMENTS

| EP | 3047810 A1 | 7/2016 |
|---|---|---|
| EP | 3560447 A1 | 10/2019 |

OTHER PUBLICATIONS

International Search Report. International Application No. PCT/IB2023/060621: Feb. 2, 2024. 4 pgs.

*Primary Examiner* — Eduardo C Robert
*Assistant Examiner* — Steven J Cotroneo
(74) *Attorney, Agent, or Firm* — Sorell, Lenna & Schmidt, LLP

(57) ABSTRACT

A spinal implant includes a first member having an arcuate portion and a second member having an arcuate portion. The first member is connected with a first portion of vertebrae and the second member is connected with a second portion of vertebrae such that the second portion of vertebrae is disposed at a first angle relative to the first portion of vertebrae in a sagittal plane of the vertebrae. A ratchet is disposed with the members such that the first member is incrementally movable relative to the second member from the first angle to a selected angle of the second portion relative to the first portion in the sagittal plane. Systems, implants and methods are disclosed.

20 Claims, 11 Drawing Sheets

(56) References Cited

U.S. PATENT DOCUMENTS

| | | | |
|---|---|---|---|
| 2009/0306717 A1* | 12/2009 | Kercher | A61B 17/7011 |
| | | | 606/279 |
| 2018/0098794 A9 | 4/2018 | Kercher et al. | |
| 2018/0125533 A1 | 5/2018 | Arnin | |
| 2019/0201058 A1* | 7/2019 | Arnin | A61B 17/7071 |
| 2022/0192710 A1 | 6/2022 | Pool | |

* cited by examiner

SPINAL CORRECTION SYSTEM AND METHOD

TECHNICAL FIELD

The present disclosure generally relates to medical devices for the treatment of spinal disorders, and more particularly to a surgical system and method for correction of a spine disorder.

BACKGROUND

Spinal disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal implants such as tethers, bone fasteners and vertebral rods can be used to provide stability to a treated region of a spine. These implants can redirect stresses away from a damaged or defective region while healing takes place to restore proper alignment and generally support the vertebral members. This disclosure describes an improvement over these prior technologies.

SUMMARY

In one embodiment, a spinal implant is provided. The spinal implant has a first member including an arcuate portion and a second member including an arcuate portion. The first member is connected with a first portion of vertebrae and the second member is connected with a second portion of vertebrae such that the second portion of vertebrae is disposed at a first angle relative to the first portion of vertebrae in a sagittal plane of the vertebrae. A ratchet is disposed with the members such that the first member is incrementally movable relative to the second member from the first angle to a selected angle of the second portion relative to the first portion in the sagittal plane. In some embodiments, systems, implants and methods are disclosed.

In some embodiments, the spinal implant includes a curved rod and a curved sleeve. The curved sleeve is connected with a first portion of vertebrae and the rod is connected with a second portion of vertebrae such that the second portion of vertebrae is disposed at a first angle relative to the first portion of vertebrae in a sagittal plane of the vertebrae. A ratchet is disposed with the sleeve and the rod such that the rod is dynamically movable relative to the sleeve from the first angle to a selected angle of the second portion relative to the first portion in the sagittal plane.

In some embodiments, a spinal implant system is provided. The spinal implant system includes a spinal implant has a first member including an arcuate portion. A second member includes an arcuate portion. A ratchet is disposed with the members. The first member is connected with a first portion of vertebrae via a first bone fastener and the second member is connected with a second portion of vertebrae via a second bone fastener such that the second portion of vertebrae is disposed at a first angle relative to the first portion of vertebrae in a sagittal plane of the vertebrae. The first member is incrementally movable relative to the first member from the first angle to a selected angle of the second portion relative to the first portion in the sagittal plane.

BRIEF DESCRIPTION OF THE DRAWINGS

The present disclosure will become more readily apparent from the specific description accompanied by the following drawings, in which.

DETAILED DESCRIPTION

Figure 1:
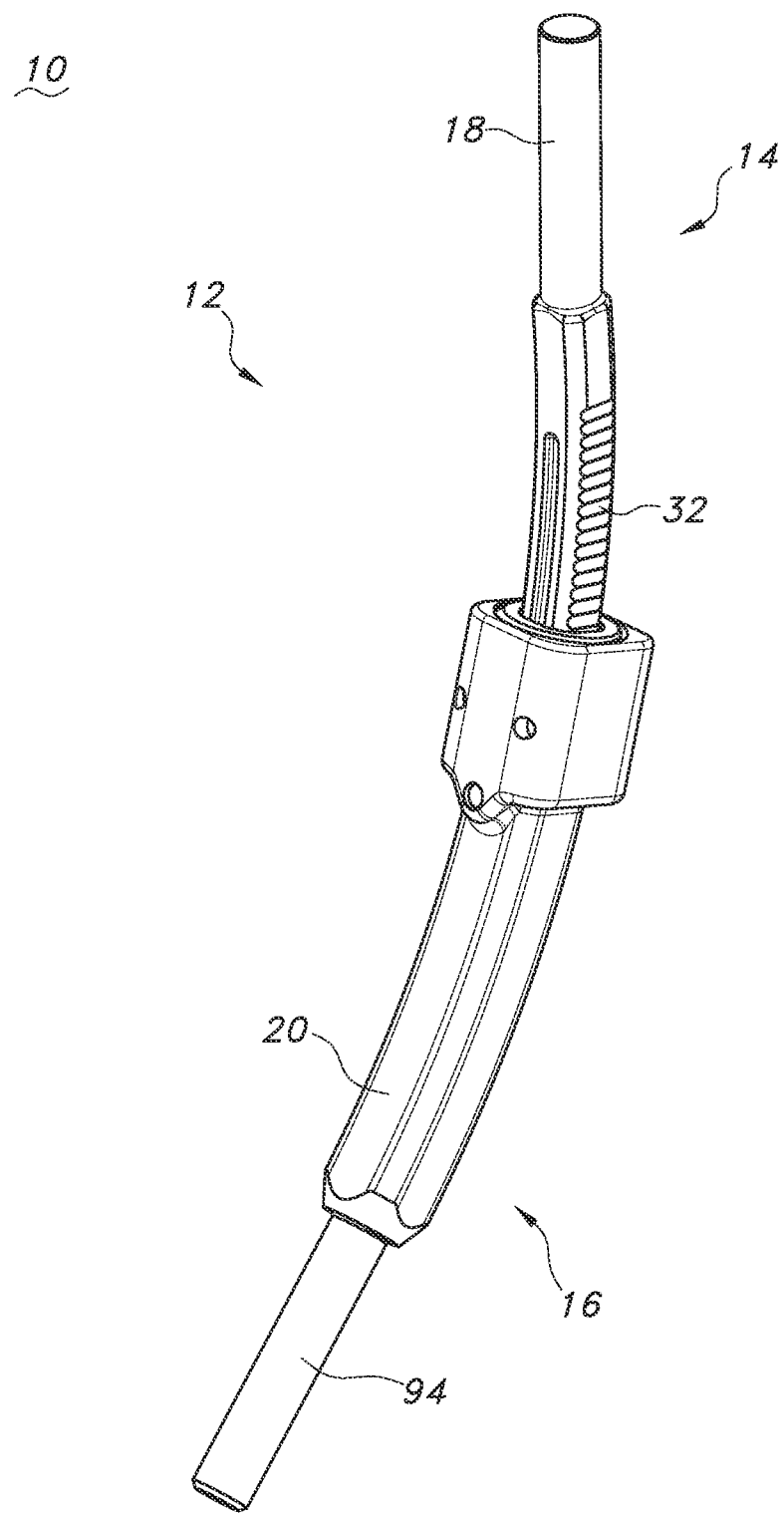
FIG. 1 is a perspective view of one embodiment of components of a surgical system in accordance with the principles of the present disclosure.

The exemplary embodiments of a surgical system and related methods of use are discussed in terms of medical devices for the treatment of musculoskeletal disorders and more particularly, in terms of a surgical system and method for correction of a spine disorder. In some embodiments, the surgical system may be employed in applications for correction of deformities, such as scoliosis and kyphosis. In some embodiments, the present surgical system includes a curved growth rod configured to incrementally extend at an angle in situ relative to a sagittal plane of a body after implantation at a surgical site in a patient to provide stabilization of the spine during growth of the patient. In some embodiments, the rod is curved such that the natural anatomic curvature of a spine is formed.

In some embodiments, the present surgical system includes a curved spinal extension rod. In some embodiments, the extension rod includes a taper lock mechanism configured to lock the extension rod at a selected length. In some embodiments, the taper lock mechanism is configured to lock the extension rod to prevent the extension rod from collapsing during normal movement of the patient. In some embodiments, an extension force is applied to a portion of the extension rod to facilitate extension of the extension rod. In some embodiments, the extension rod is configured for use in pediatric patients to provide stabilization to the spine during growth of the patient. In some embodiments, the extension rod is configured for implantation at a surgical site including a portion of the spine of the patient and is configured to incrementally extend in situ during growth of the patient. In some embodiments, the extension rod is configured to extend in situ without the need for multiple surgeries to extend the rod. In some embodiments, the extension rod is configured to extend at an angle to align with the natural curvature of the spine in the sagittal plane. In some embodiments, the extension rod facilitates spinal growth into a natural anatomic curvature. In some embodiments, the extension rod enables increased sagittal balance for the patient and improves growth. In some embodiments, the extension rod is implanted in procedures for the treatment of scoliosis.

In some embodiments, the present surgical system includes a curved spinal extension rod that is connected with vertebrae via bone fasteners. In some embodiments, the bone fasteners include spinal screws and/or spinal hooks. In some embodiments, the extension rod includes ends configured for attachment to the spinal screws or hooks. In some embodiments, the extension rod is configured to extend during growth of the patient. In some embodiments, the extension rod includes an extension section, for example, a rod and a sleeve. In some embodiments, the rod and the sleeve are curved to simulate the natural sagittal curvature of the spine. In some embodiments, an angle between the ends of the extension rod changes as the extension rod extends. In some embodiments, the extension rod is positioned between a collapsed orientation and a fully extended orientation. In some embodiments, an angle between the collapsed orientation and the fully extended orientation can vary. In some embodiments, the angle between the collapsed orientation and the fully extended orientation includes a 40 degree angle. In some embodiments, the extension rod is configured to correct a spine of a patient such that the spine is adjusted to have a 40 degree curvature at the end of full expansion of the extension rod, paralleling the natural sagittal curvature of the thoracic spine.

In some embodiments, the present surgical system includes a curved spinal extension rod including a curved rod and a curved sleeve. In some embodiments, a portion of the curved rod is configured for disposal within the curved sleeve. In some embodiments, the curved sleeve is manufactured from a three dimensional (3D) printed metal component, and the curved rod is manufactured from a machining process, for example, computerized numerical control (CNC) machining. In some embodiments, extension rod includes a fixed end configured for engagement with an end of the curved sleeve. In some embodiments, the fixed end and the curved sleeve are a single monolithic piece. In some embodiments, the curved sleeve includes a limit pin configured for engagement with a slot on the curved rod to maintain assembly of the curved rod with the curved sleeve. In some embodiments, the curved rod includes a plurality of grooves configured for engagement with locking pins. In some embodiments, the extension rod includes a screw, a biasing member including a spring, a collar and one or more locking pins. In some embodiments, the extension rod includes a pair of locking pins. In some embodiments, the extension rod includes a taper lock mechanism configured to lock the extension rod at a selected length. In some embodiments, the taper lock mechanism includes a biasing member including a spring. In some embodiments, the spring exerts a selected amount of force on the collar to prevent the taper lock mechanism from sliding such that the length of the extension rod does not incrementally adjust without extension force being applied to the extension rod. In some embodiments, the curved sleeve incudes a pair of tapered slots, including the locking pins, and a compressive force is applied to the curved rod to cause the locking pins to wedge between the tapered slots and the curved rod, thereby locking the curved rod with the sleeve and preventing the extension rod from collapsing during normal movement of the patient. In some embodiments, an extension force is applied to the curved rod to facilitate extension of the extension rod. In some embodiments, the curved sleeve includes a pair of openings configured for assembling the locking pins with the extension rod such that the locking pins are disposed with an inner surface of the curved sleeve. In some embodiments, a surgical tool can be inserted into openings to disengage the lock mechanism. In some embodiments, the surgical tool is configured to engage and apply a force, for example, an upward force on the collar to disengage the lock mechanism.

In some embodiments, the present surgical system includes a curved spinal extension rod including a curved rod and a curved sleeve having a pawl, for example, a spring loaded pawl configured to lock the curved rod with the curved sleeve. In some embodiments, the curved rod defines a plurality of teeth or a plurality of grooves. In some embodiments, the spring loaded pawl is configured to engage the plurality of teeth or the plurality of grooves. In some embodiments, the curved sleeve includes a cam, for example, a spring loaded cam configured to engage with the curved rod. In some embodiments, the curved rod does not include a plurality of teeth or a plurality of grooves to engage with the spring loaded cam.

In some embodiments, the present surgical system is employed with a method for treating a spinal disorder in a patient. In some embodiments, the method includes the step of fixing a bone fastener with a first portion of vertebrae and fixing a second bone fastener with a second portion of vertebrae. In some embodiments, the method includes the step of fixing a spinal implant with the bone fasteners. In some embodiments, the spinal implant includes a rod including an arcuate portion, a sleeve including an arcuate portion, and a ratchet disposed with the sleeve and the rod. In some embodiments, the spinal implant is fixed with the bone fasteners such that the second portion of vertebrae is disposed at a first angle relative to the portion of vertebrae in a sagittal plane of the vertebrae. In some embodiments, the rod is incrementally movable relative to the sleeve from the first angle to a selected angle of the second portion relative to the first portion in the sagittal plane. In some embodiments, the present system and/or method provide incremental adjustment such that the spine of the patient is corrected to have a 40 degree curvature, paralleling the natural sagittal curvature of the thoracic spine.

In some embodiments, the present surgical system is configured for use with surgical navigation, for example, fluoroscope or image guidance. In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or anterolateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-15, there are illustrated components of a surgical system, for example, a spinal correction system 10.

The components of spinal correction system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Figure 2:
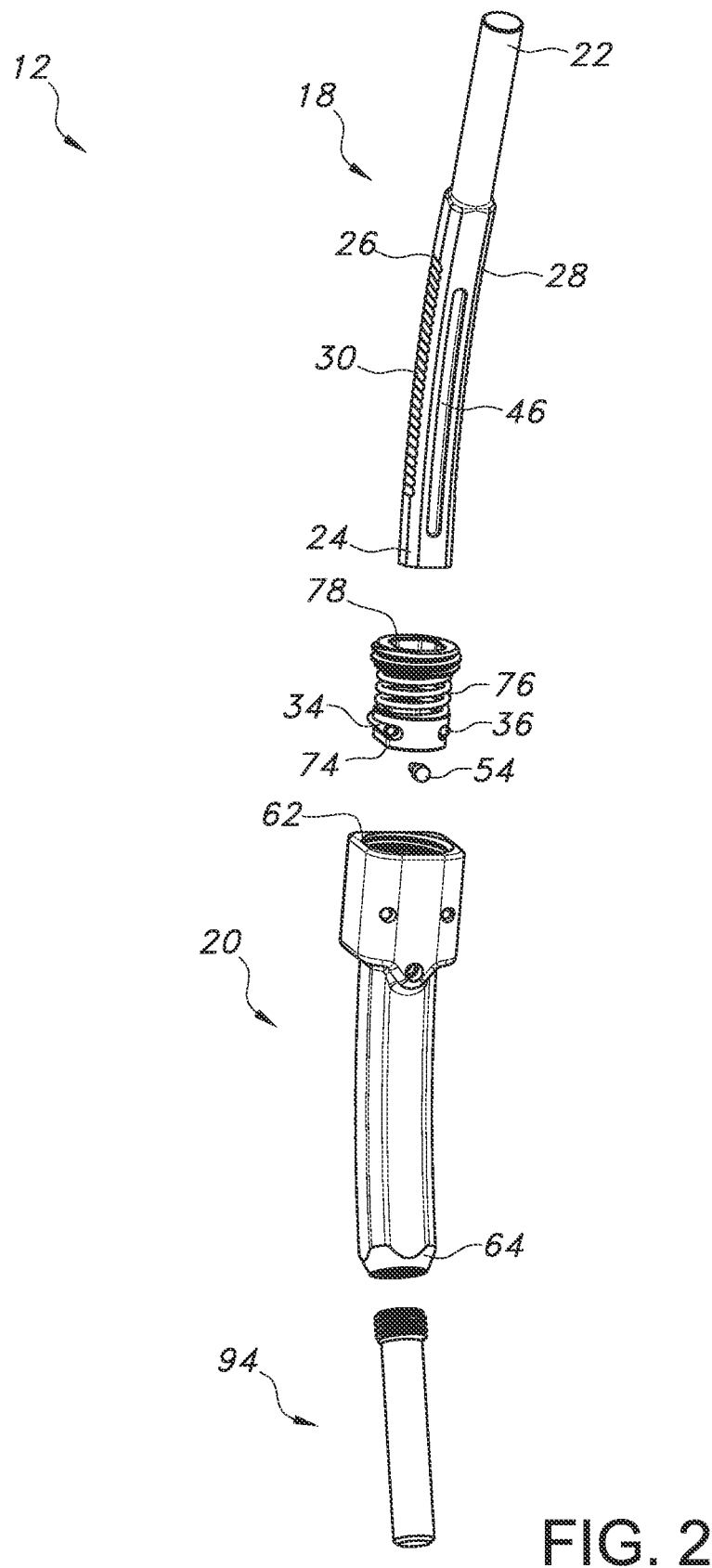
FIG. 2 is a perspective view of the components shown in FIG. 1 with parts separated.

Spinal correction system 10 includes a spinal implant, for example, a growth rod 12, shown in FIGS. 1 and 2. Growth rod 12 is configured to extend at an angle relative to a sagittal plane of a patient after implantation at a surgical site to provide stabilization of the spine during growth of the patient. In some embodiments, growth rod 12 is configured to incrementally extend at an angle in situ relative to a sagittal plane. In some embodiments, growth rod 12 is curved such that natural anatomic curvature found in a healthy spine is formed in the patient. Growth rod 12 extends between an end 14, an end 16, and defines a longitudinal axis AA (shown in FIG. 8). End 14 includes a member, for example, a rod 18 and end 16 includes a member, for example, a sleeve 20.

Rod 18 extends between an end 22 and an end 24. End 22 is configured for connection with a portion of vertebrae via a bone fastener 100a, described herein. End 24 is configured for disposal with sleeve 20 and is incrementally movable relative to sleeve 20 via a ratchet 27, shown in FIG. 6. In some embodiments, a portion of rod 18 is disposed in a telescopic configuration with sleeve 20. In some embodiments, rod 18 is dynamically expandable in situ in an outward direction sleeve 20, as described herein.

Rod 18 is curved and includes an arcuate portion. Rod 18 includes a side 26 and an opposing side 28. An outer surface of side 26 defines a portion of ratchet 27 including a plurality of grooves 30, and side 28 defines a portion of ratchet 27 including a plurality of grooves 32. Grooves 30, 32 are transverse grooves. Grooves 30, 32 are configured for engagement with a portion of ratchet 27 including a pair of pins 34, 36 that are configured for disposal with tapered slots 38, 40 of sleeve 20, for incremental adjustment of rod 18 relative to sleeve 20, as described herein. Pins 34, 36 are disposable in an expandable orientation with tapered slots 38, 40 to allow movement of rod 18 in a direction, for example, an upward or outward direction, shown by arrow A in FIG. 7, relative to sleeve 20, and pins 34, 36 are disposable in a locked orientation with tapered slots 38, 40 to prevent movement and collapse of rod 18 in an opposite direction, for example, a downward or inward direction, shown by arrow B in FIG. 7, relative to sleeve 20. In some embodiments, grooves 30, 32 may have alternate surface configurations to enhance engagement with pins 34, 36, for example rough, threaded, arcuate, undulating, porous, semi-porous, dimpled, polished and/or textured. In some embodiments, sides 26, 28 do not include grooves 30, 32 and rod 18 can incrementally adjust relative to sleeve 20 via tension.

Figure 3:
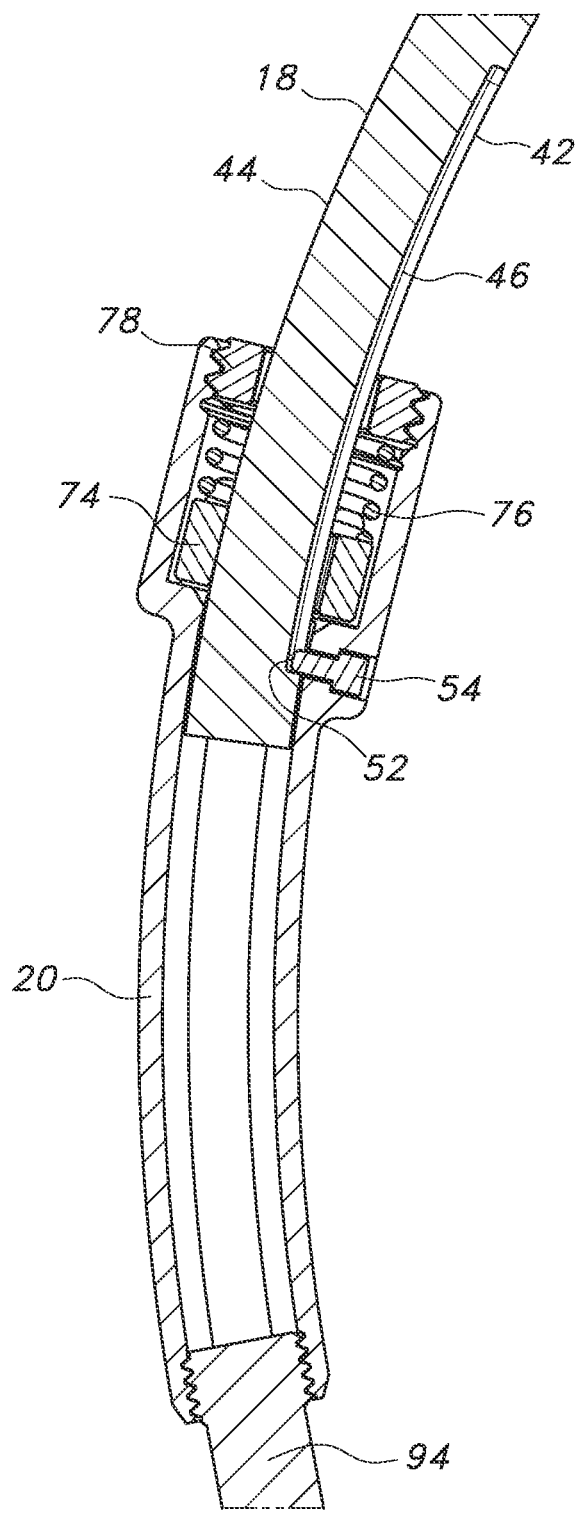
FIG. 3 is a break away cross section view of components of the system shown in FIG. 1.
Figure 4:
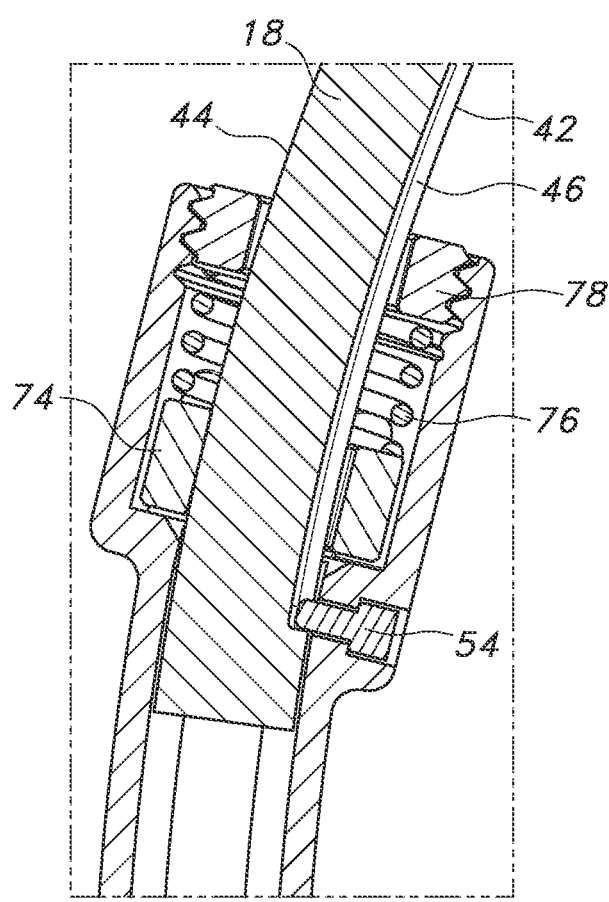
FIG. 4 is a break away cross section view of components of the system shown in FIG. 1.
Figure 5:
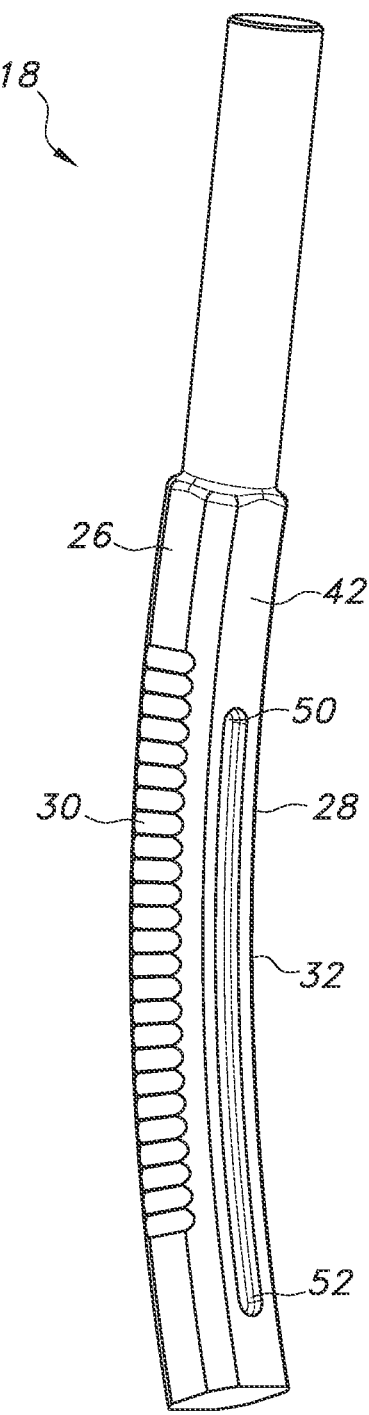
FIG. 5 is a perspective view of components of the system shown in FIG. 1.

Rod 18 includes a side 42 and an opposing side 44, as shown in FIGS. 3-5. Side 42 includes an outer surface defining an axial slot 46. Slot 46 is configured as a stop to limit translation of rod 18 relative to sleeve 20. Slot 46 includes an end 50 that defines a translation limit and an end 52 that defines a translation limit for a pin 54 disposed with sleeve 20. Rod 18 is movable relative to sleeve 20 between a limit defined from end 50 to end 52 via pin 54. In some embodiments, slot 46 and pin 54 are configured to movably fix rod 18 and sleeve 20 such that rod and sleeve are maintained in an assembled configuration. In some embodiments, slot 46 may have alternate surface configurations to enhance engagement with pin 54 for example rough, threaded, arcuate, undulating, porous, semi-porous, dimpled, polished and/or textured.

Sleeve 20 extends between an end 62 and an end 64, shown in FIG. 2. End 62 is configured for engagement with end 24 of rod 18. End 64 is configured for connection with a portion of vertebrae via a bone fastener 100b, described herein. Sleeve 20 is curved and includes an arcuate portion. Sleeve 20 is configured for connection with a portion of vertebrae, which is disposed at an angle $\alpha 1$ (FIG. 8) relative to axis AA and relative to the portion of vertebrae connected with rod 18. In some embodiments, angle $\alpha 1$ is disposed in a sagittal plane of the vertebrae, as described herein.

Figure 7:
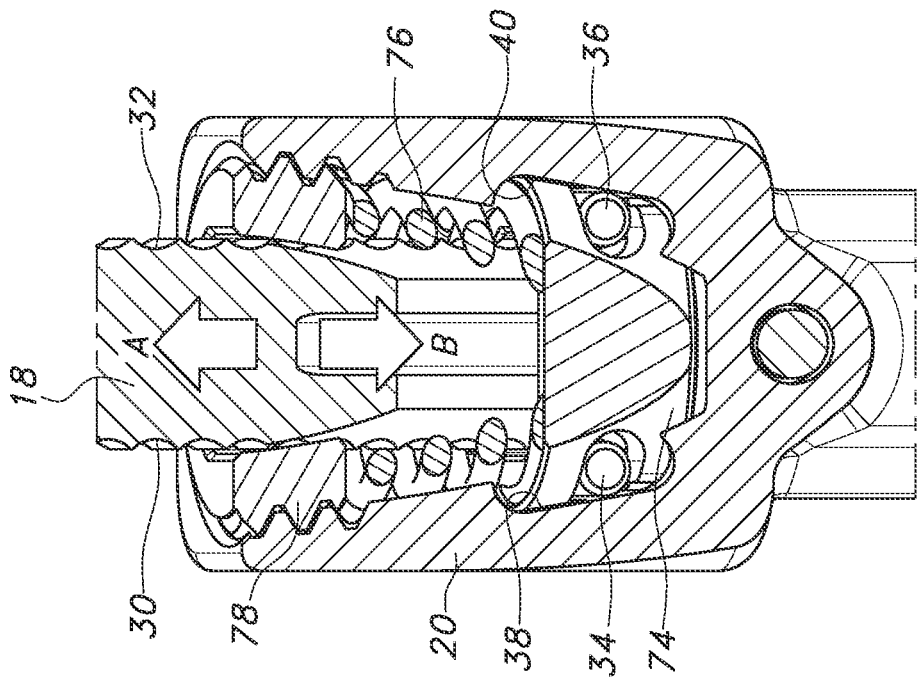
FIG. 7 is a break away cross section view of components of the system shown in FIG. 1.
Figure 6:
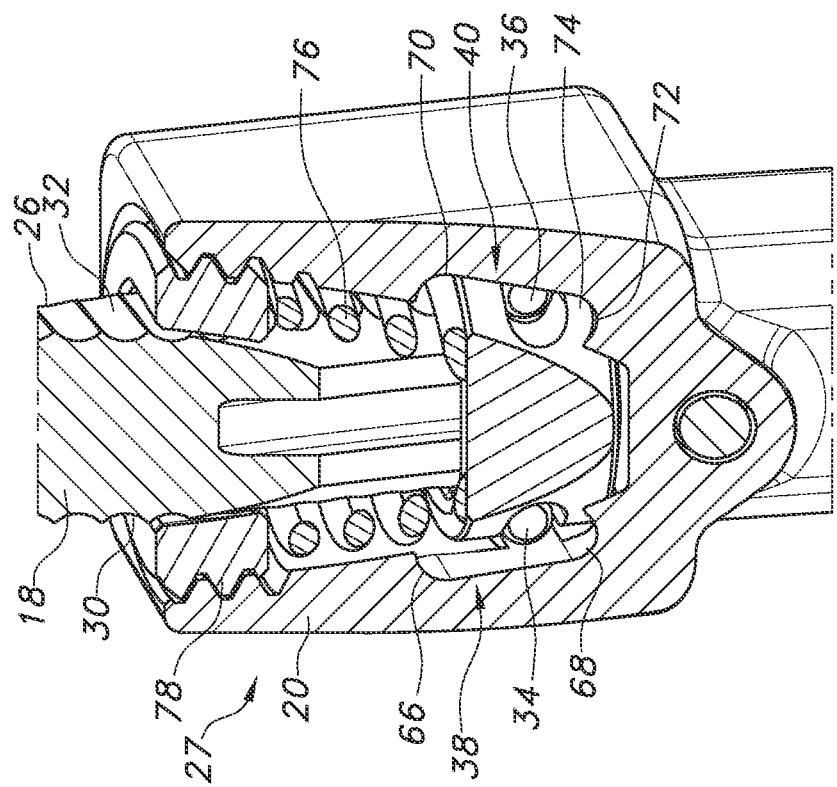
FIG. 6 is a break away cross section view of components of the system shown in FIG. 1.

Sleeve 20 includes a portion of ratchet 27 including tapered slots 38, 40 configured for engagement with pins 34, 36 that engage grooves 30, 32 for incremental adjustment of rod 18 relative to sleeve 20, shown in FIGS. 6 and 7, as described herein. Ratchet 27 is configured to incrementally move rod 18 relative to sleeve 20 from angle $\alpha 1$ to a selected angle $\alpha 2$ (FIG. 9) relative to axis AA, disposed in a selected plane of the vertebrae. In some embodiments, ratchet 27 is configured to incrementally move rod 18 relative to sleeve 20 from angle $\alpha 1$ to the selected angle $\alpha 2$ relative to axis AA, disposed in the sagittal plane of the vertebrae. In some embodiments, the selected angle $\alpha 2$ is in a range of 1 through 40 angular degrees. Slot 38 includes an end 66 and an end 68 configured for engagement with pin 34. Slot 40 includes an end 70 and an end 72 configured for engagement with pin 36.

A collar 74 is configured for engagement with slots 38, 40, pins 34, 36, and is disposed about rod 18. A biasing member, for example, a spring 76 is configured for engagement with collar 74 and is configured for disposal about rod 18. A screw 78 is configured for threaded engagement with end 62 of sleeve 20. Spring 76 is configured for engagement with a portion of screw 78 and rod 18, and is configured for disposal with screw 78.

Figure 8:
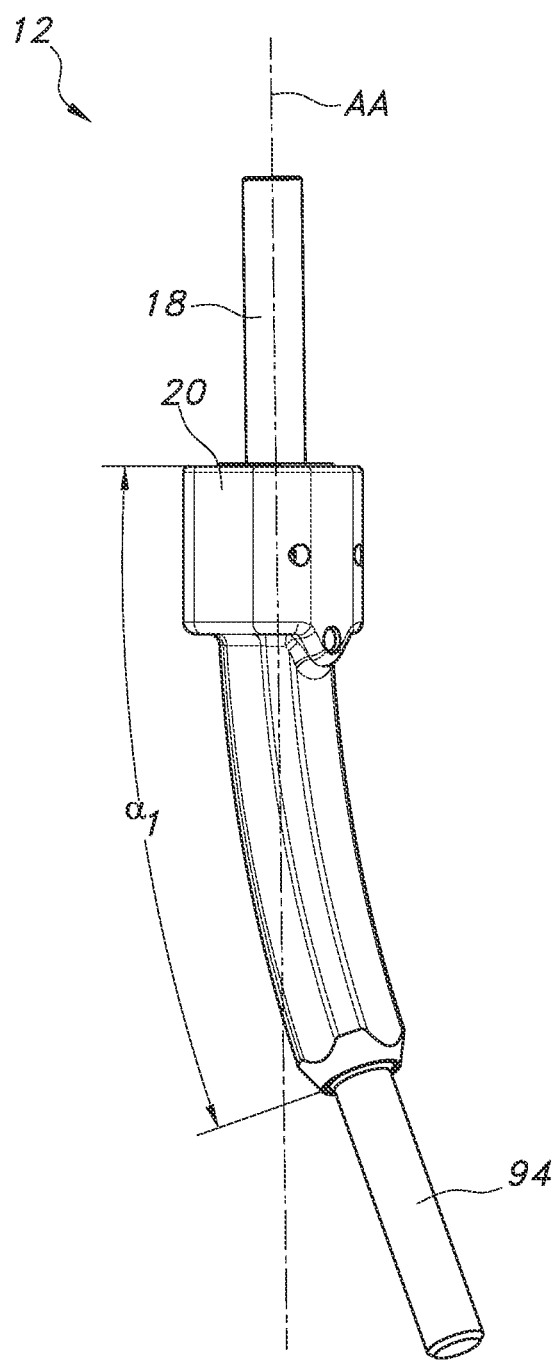
FIG. 8 is a perspective view of the components of the system shown in FIG. 1.
Figure 9:
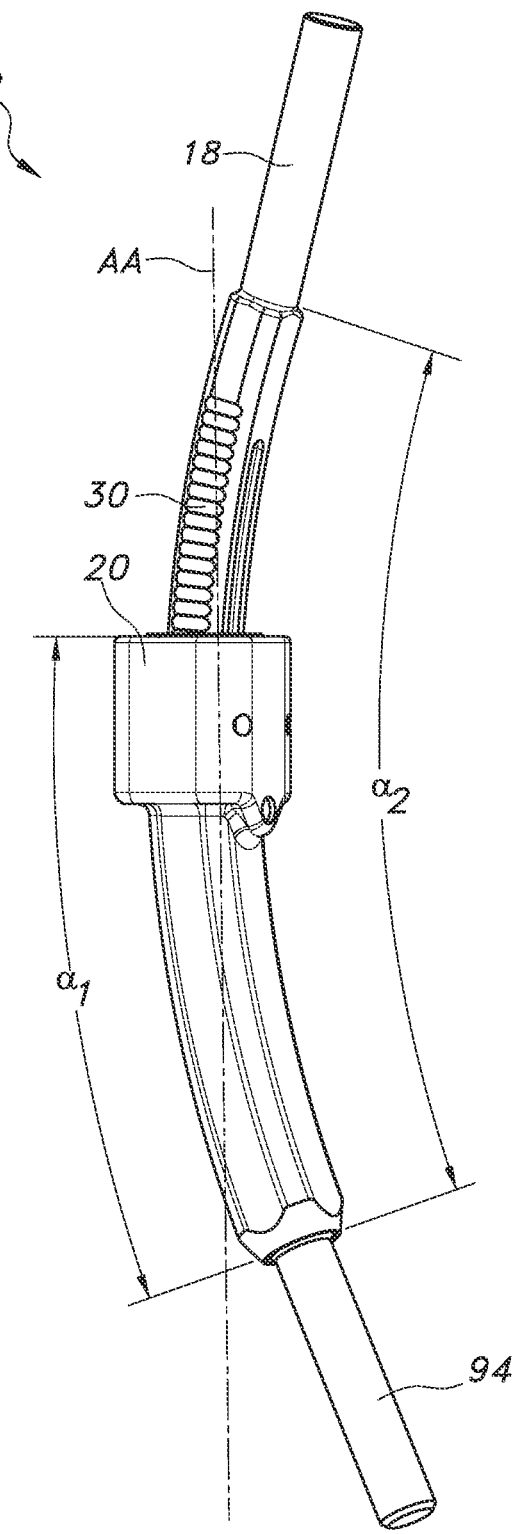
FIG. 9 is a perspective view of the components of the system shown in FIG. 1.
Figure 10:
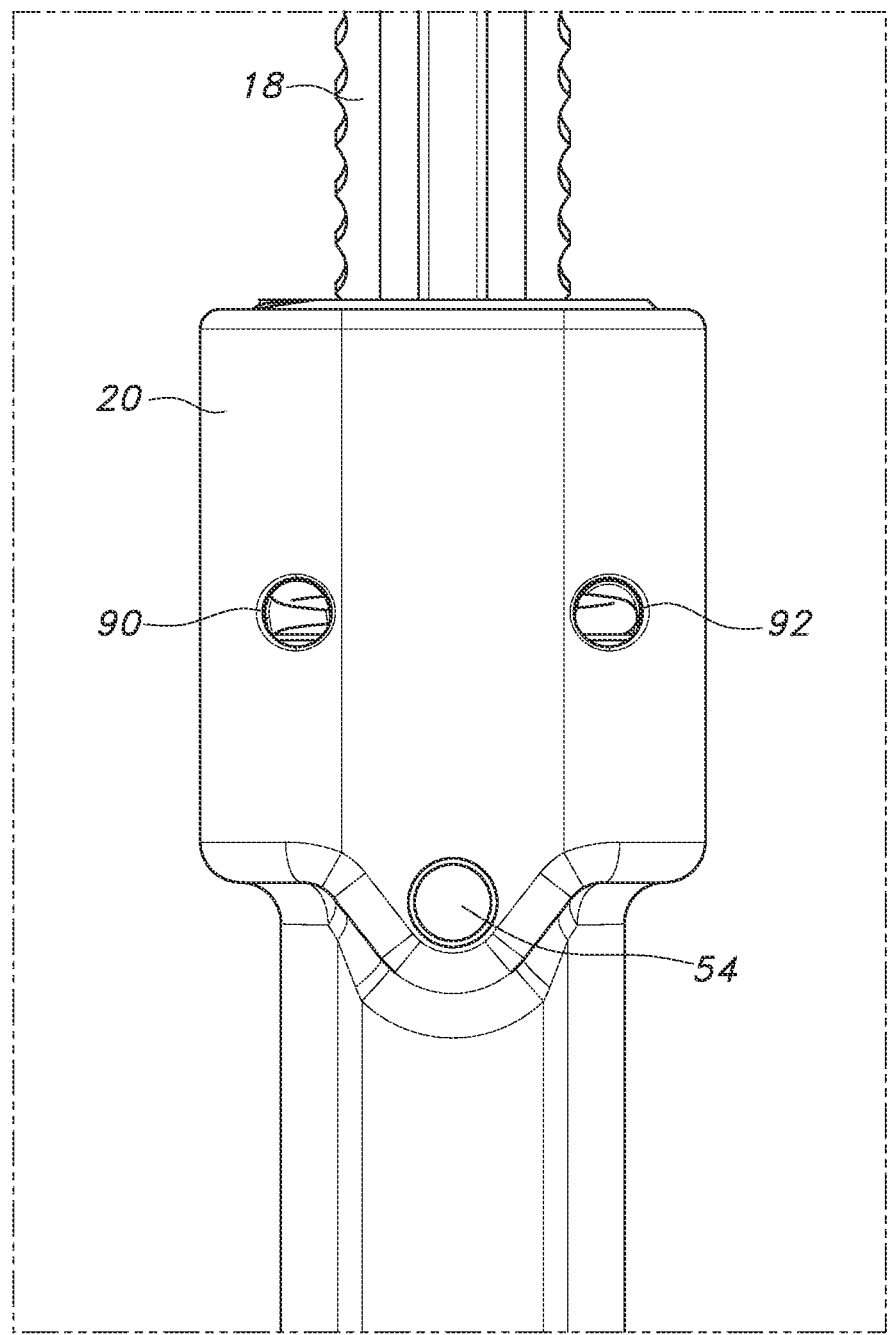
FIG. 10 is a break away plan view of components of the system shown in FIG. 1.

Pins 34, 36 are disposable in the expandable orientation with tapered slots 38, 40 to allow movement of rod 18 in the upward or outward direction relative to sleeve 20, as shown in FIG. 9, and pins 34, 36 are disposable in the locked orientation with tapered slots 38, 40 to prevent movement and collapse of rod 18 in an opposite direction, for example, a downward or inward direction relative to sleeve 20, as shown in FIG. 8. In the expandable orientation, an extension force, for example, force applied during traction of the patient, facilitates extension of rod 18 in situ. In the locked orientation, spring 76 exerts a selected amount of force on collar 74 to prevent rod 18 from moving, for example, during normal movement of the patient. In the locked orientation, a compressive force via spring 76 applied to rod 18 causes pins 34, 36 to wedge between tapered slots 38, 40, thereby locking rod 18 with sleeve 20. In some embodiments, rod 18 and sleeve 20 are biased to maintain pins 34, 36 in the locked orientation.

Figure 13:
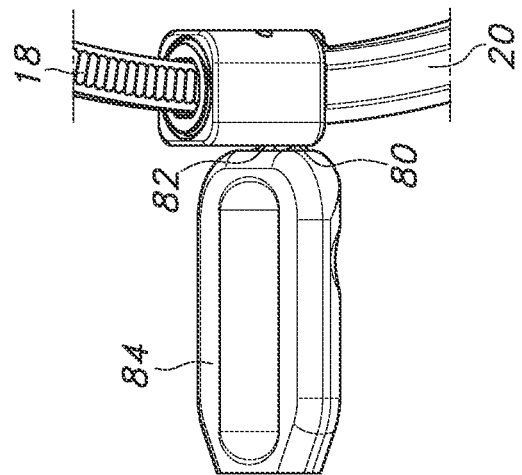
FIG. 13 is a break away view of components of the system shown in FIG. 11.
Figure 11:
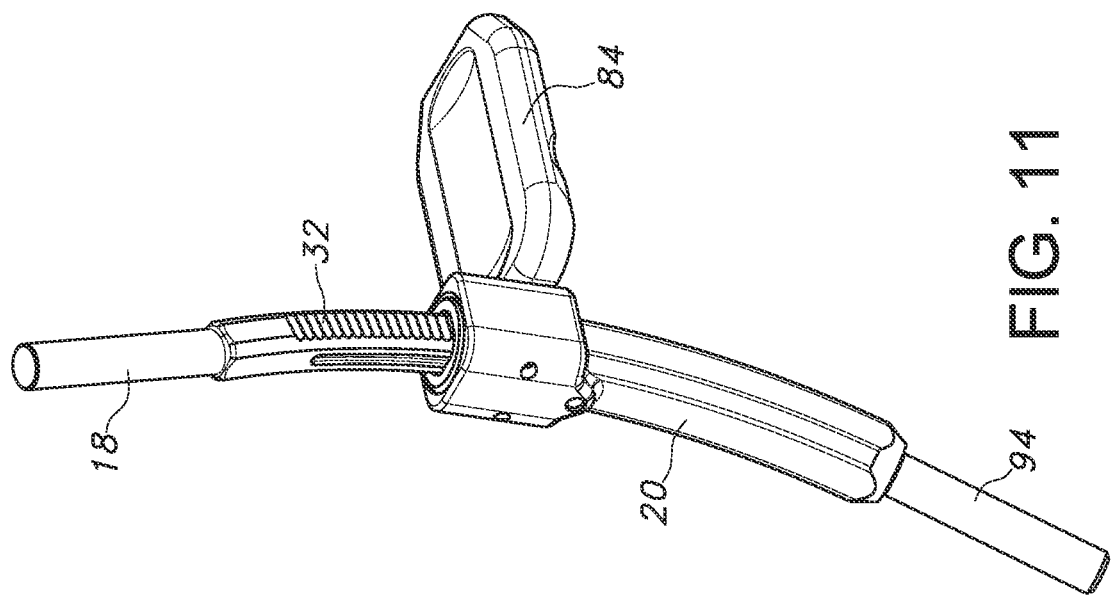
FIG. 11 is a perspective view of one embodiment of components of a surgical system in accordance with the principles of the present disclosure.
Figure 12:
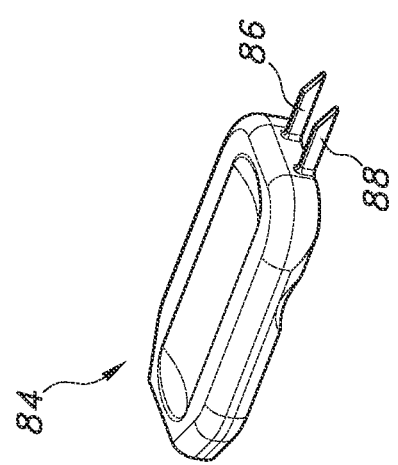
FIG. 12 is a perspective view of components of the system shown in FIG. 11.
Figure 14:
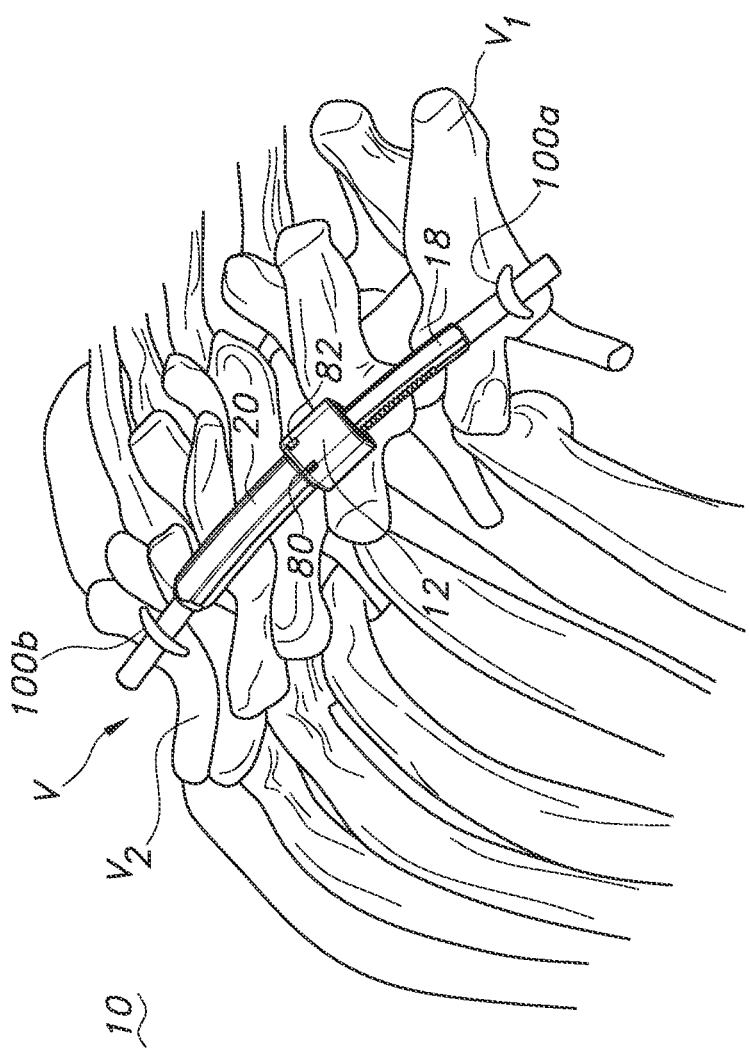
FIG. 14 is a perspective view of one embodiment of components of a surgical system in accordance with the principles of the present disclosure disposed with vertebrae.

An outer surface of sleeve 20 defines openings 80, 82 configured for engagement with a surgical tool 84, as shown in FIGS. 13 and 14. Tool 84 includes tongs 86, 88 that are configured for disposal within openings 80, 82 to disengage and unlock rod 18 via engagement with collar 74. Tool 84 is configured to apply a force, for example, an upward force on collar 74 to disengage rod 18. The outer surface of sleeve 20 defines openings 90, 92 that are configured for engagement with pins 34, 36 such that pins 34, 36 can be assembled with growth rod 12.

End 64 of sleeve 20 is configured for threaded engagement with a straight rod 94, shown in FIG. 2. In some embodiments, end 64 and rod 94 are a single monolithic piece. In some embodiments, rod 94 may comprise overall and/or cross-section configurations, for example, cylindrical, round, oval, rectangular, polygonal, irregular, tapered, offset, staggered, uniform and non-uniform.

In some embodiments, rod 18 is configured for connection with a portion of vertebrae via bone fastener 100a, and sleeve 20 is configured for connection with a portion of vertebrae via bone fastener 100b, shown in FIG. 14. In some embodiments, bone fasteners 100a, 100b include spinal screws and/or spinal hooks. In some embodiments, spinal correction system 10 can include one or a plurality of bone fasteners 100a, 100b such as those described herein and/or fixation elements, which may be employed with a single vertebral level or a plurality of vertebral levels. In some embodiments, bone fasteners 100a, 100b may be engaged with vertebrae in various orientations, for example, series, parallel, offset, staggered and/or alternate vertebral levels. In some embodiments, bone fasteners 100a, 100b may be configured as multi-axial screws, sagittal angulation screws, pedicle screws, mono-axial screws, uni-planar screws, fixed screws, anchors, tissue penetrating screws, conventional screws, expanding screws. In some embodiments, bone fasteners 100a, 100b may be employed with wedges, anchors, buttons, clips, snaps, friction fittings, compressive fittings, expanding rivets, staples, nails, adhesives, posts, connectors, fixation plates and/or post.

In assembly, operation and use, spinal correction system 10, similar to the systems and methods described herein, is employed with a surgical procedure, such as, for example, a correction treatment of an affected portion of a spine, which may, for example, include a correction treatment to treat adolescent idiopathic scoliosis and/or Scheuermann's kyphosis of a spine. In some embodiments, one or all of the components of spinal correction system 10 can be delivered or implanted as a pre-assembled device or can be assembled in situ. Spinal correction system 10 may be completely or partially revised, removed or replaced.

Figure 15:
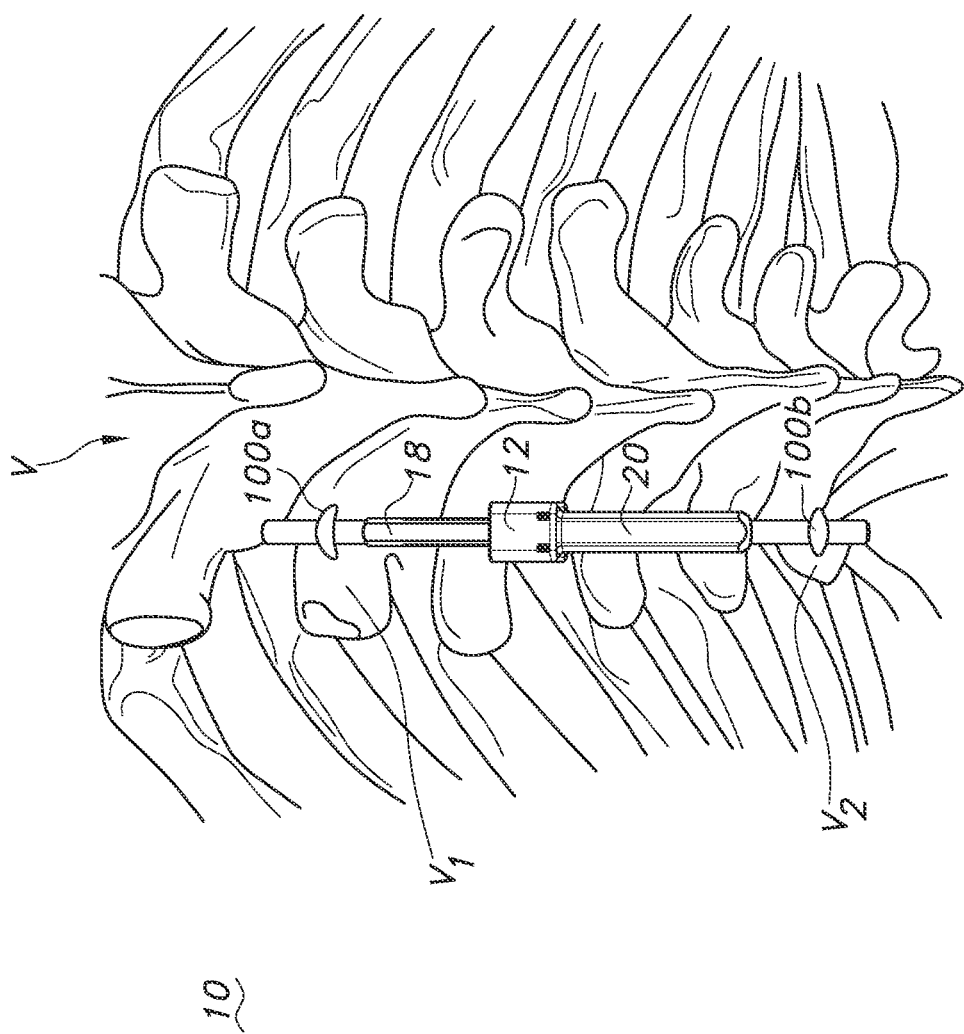
FIG. 15 is a perspective view of one embodiment of components of a surgical system in accordance with the principles of the present disclosure disposed with vertebrae.

In use, to treat a selected section of vertebrae V, as shown in FIGS. 14 and 15, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region.

Growth rod 12 is delivered along the surgical pathway to a surgical site. End 22 of rod 18 is fixed with vertebra V1 via bone fastener 100a and end 64 of sleeve 20 is fixed with vertebra V2 via bone fastener 100b. Growth rod 12 is fixed to the surgical site in a collapsible orientation at angle $\alpha 1$. During growth of the patient, growth rod 12 is configured to incrementally expand in situ via components of ratchet 27, described herein such that angle $\alpha 1$ is expandable to angle $\alpha 2$ via expansion of rod 18 relative to sleeve 20 such that the spine of the patient is corrected. In some embodiments, angle $\alpha 1$ is expandable to angle $\alpha 2$ such that the spine of the patient is corrected to angle $\alpha 2$, which may include an angle in a range of 1 through 40 angular degrees, and for example, a 40 degree curvature, paralleling the natural sagittal curvature of the thoracic spine. In some embodiments, an extension force is applied to growth rod 12, including force applied during traction of the patient, to facilitate expansion of rod 18 relative to sleeve 20.

In some embodiments, growth rod 12 is configured to extend in situ without the need for multiple surgeries to extend growth rod 12. In some embodiments, rod 18 is configured to extend to an angle $\alpha 2$ to align with the natural curvature of the spine in the sagittal plane. In some embodiments, growth rod 12 facilitates spinal growth into a natural anatomic curvature.

Upon completion of the procedure, the surgical instruments, assemblies and non-implanted components of spinal correction system 10 are removed from the surgical site and the incision is closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10.

In some embodiments, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 may be used to prevent or minimize curve progression in individuals of various ages.

Figure 16:
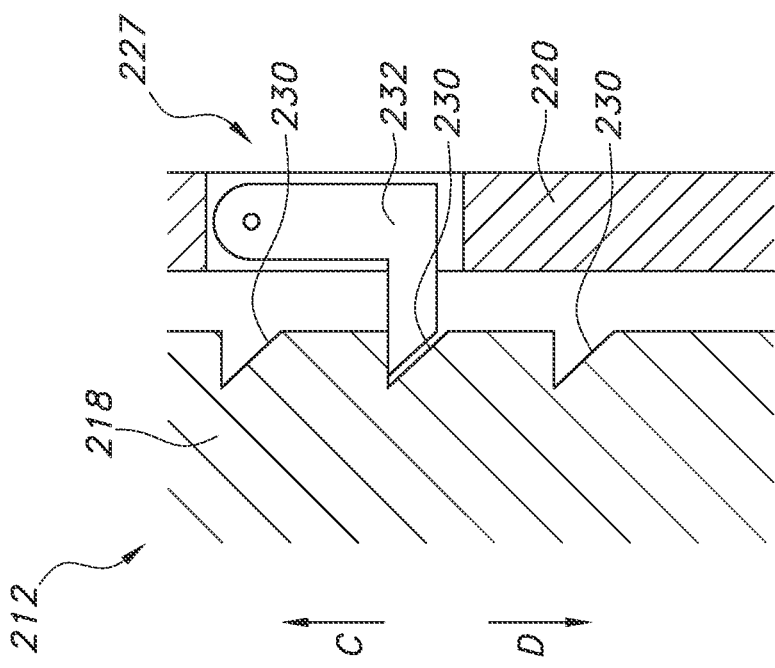
FIG. 16 is a break away cross section view of one embodiment of components of a surgical system in accordance with the principles of the present disclosure.

In one embodiment, as shown in FIG. 16, spinal correction system 10, similar to the systems and methods described above with regard to FIGS. 1-15, includes a growth rod 212, similar to growth rod 12 described herein. Growth rod 212 includes a member, for example, a rod 218, similar to rod 18 described herein, and a member, for example, a sleeve 220, similar to sleeve 20 described herein. Rod 218 and sleeve 220 are curved. Rod 218 is configured for disposal with sleeve 220 and is incrementally movable relative to sleeve 220 via a ratchet 227.

Rod 218 includes an outer surface that defines a plurality of teeth 230 configured for engagement with a spring loaded pawl 232 disposed within an inner surface of sleeve 220. Teeth 230 and pawl 232 form ratchet 227. Engagement of teeth 230 and pawl 232 is configured for incremental adjustment of rod 218 relative to sleeve 220, similar to that described herein. Rod 212 is configured for disposal in an expandable orientation, similar to that described herein, to allow movement of rod 218 in a direction, for example, an upward or outward direction, shown by arrow C in FIG. 16, relative to sleeve 220, and rod 212 is disposable in a locked orientation, similar to that described herein, to prevent movement and collapse of rod 218 in an opposite direction, for example, a downward or inward direction, shown by arrow D in FIG. 16, relative to sleeve 220. In some embodiments, teeth 230 alternatively include a plurality of grooves configured for engagement with pawl 232. In some embodiments, sleeve 220 includes a plurality of pawls 232.

Figure 17:
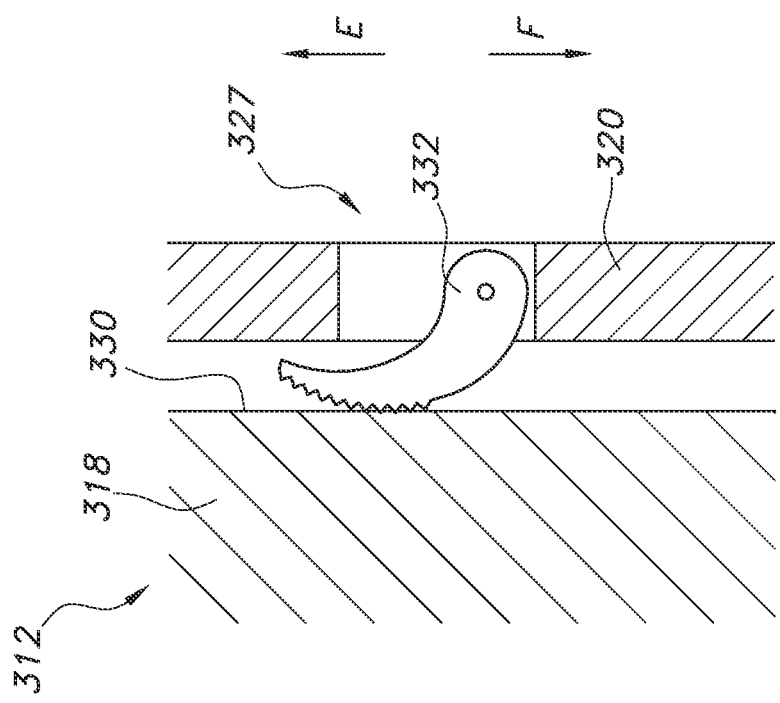
FIG. 17 is a break away cross section view of one embodiment of components of a surgical system in accordance with the principles of the present disclosure.

In one embodiment, as shown in FIG. 17, spinal correction system 10, similar to the systems and methods described above with regard to FIGS. 1-15, includes a growth rod 312, similar to growth rod 12 described herein. Growth rod 312 includes a member, for example, a rod 318, similar to rod 18 described herein, and a member, for example, a sleeve 320, similar to sleeve 20 described herein. Rod 318 and sleeve 320 are curved. Rod 318 is configured for disposal with sleeve 320 and is incrementally movable relative to sleeve 320 via a ratchet 327.

Rod 318 includes an outer surface 330 configured for engagement with a biased cam 332 disposed within an inner surface of sleeve 320. Surface 330 and cam 332 form ratchet 327. Engagement of surface 330 and cam 332 is configured for incremental adjustment of rod 318 relative to sleeve 320. Rod 312 is configured for disposal in an expandable orientation, similar to that described herein, to allow movement of rod 318 in a direction, for example, an upward or outward direction, shown by arrow E in FIG. 17, relative to sleeve 320, and rod 312 is disposable in a locked orientation, similar to that described herein, to prevent movement and collapse of rod 318 in an opposite direction, for example, a downward or inward direction, shown by arrow F in FIG. 17, relative to sleeve 320. In some embodiments, surface 330 may include a plurality of teeth or grooves configured for engagement with cam 332. In some embodiments, sleeve 320 includes a plurality of cams 332.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
    a first member defining a longitudinal axis and including a rod, an arcuate portion and a plurality of transverse grooves;
    a second member including a rod, an arcuate sleeve and a surface defining at least one longitudinal slot, the rod of the first member being configured for fixation with a posterior surface of a first vertebra via a bone fastener and the rod of the second member being configured for fixation with a posterior surface of a second vertebra via a bone fastener such that the second vertebra is disposed at a first angle relative to the first vertebra in a sagittal plane of the vertebrae; and
    a ratchet disposed with the members such that the first member is incrementally movable relative to the second member from the first angle to a selected angle of the second vertebra relative to the first vertebra in the sagittal plane,
    the ratchet including the at least one longitudinal slot and the plurality of transverse grooves,
    in an expandable orientation a first pin is disposed in the at least one longitudinal slot to allow expansion of the first member in a first direction relative to the second member, and
    in a locked orientation the first pin is longitudinally biased into locking engagement with the surface and one of the plurality of transverse grooves to prevent movement of the first member relative to the second member in a second opposite direction.

2. A spinal implant as recited in claim 1, wherein the at least one longitudinal slot includes a tapered slot such that the locking engagement includes the first pin being wedge fit with the surface and the transverse groove.

3. A spinal implant as recited in claim 1, further comprising a spring disposed with the members to maintain the first pin in the locked orientation.

4. A spinal implant as recited in claim 1, further comprising a collar including the first pin and a second pin disposed about the first member.

5. A spinal implant as recited in claim 1, wherein the members are relatively movable between a first selected limit and a second selected limit.

6. A spinal implant as recited in claim 5, wherein the first member includes at least one groove and the second member includes at least one stop engageable to define at least one of the first limit or the second limit.

7. A spinal implant as recited in claim 1, wherein the members are dynamically expandable in situ in a first direction.

8. A spinal implant as recited in claim 1, wherein the selected angle is in a range of 1 through 40 angular degrees.

9. A spinal implant as recited in claim 1, wherein a portion of the first member is disposed in a telescopic configuration with the second member.

10. A spinal implant as recited in claim 1, further comprising a collar defining a transverse cavity for disposal of the first pin, and a biasing member engageable with the collar to fix the first pin in the locked orientation.

11. A spinal implant as recited in claim 1, wherein the second member includes a surface defining a second longitudinal slot configured for disposal of a second pin.

12. A spinal implant comprising:
    a curved rod defining a longitudinal axis and a plurality of transverse grooves;
    a curved sleeve including a rod, a surface defining a first longitudinal slot and a surface defining a second longitudinal slot, the rod of the sleeve being configured for fixation with a posterior surface of a first vertebra via a bone fastener and an end of the curved rod being configured for fixation with a posterior surface of a second vertebra via a bone fastener such that the second vertebra is disposed at a first angle relative to the first vertebra in a sagittal plane of the vertebrae; and
    a ratchet disposed with the sleeve and the rod such that the rod is dynamically movable relative to the sleeve from the first angle to a selected angle of the second vertebra relative to the first vertebra in the sagittal plane,
    the ratchet including the slots and the grooves,
    in an expandable orientation a first pin is disposed in the first slot and a second pin is disposed in the second slot to allow expansion of the rod in a first direction relative to the sleeve, and
    in a locked orientation the pins are longitudinally biased into locking engagement with the slot surfaces and the grooves to prevent movement of the rod relative to the sleeve in a second opposite direction.

13. A spinal implant as recited in claim 12, wherein the first longitudinal slot and the second longitudinal slot each include a tapered slot configured for disposal of the first pin and the second pin respectively, and the rod includes the plurality of transverse grooves such that the sleeve and the rod are incrementally expandable.

14. A spinal implant as recited in claim 12, further comprising a collar including the first pin and the second pin disposed about the rod.

15. A spinal implant as recited in claim 12, wherein the sleeve and the rod are relatively movable between a first selected limit and a second selected limit, the rod including at least one groove and the sleeve including at least one stop engageable to define at least one of the first limit or the second limit.

16. A spinal implant as recited in claim 12, further comprising a collar defining a first transverse cavity and a second transverse cavity configured for disposal of the first pin and the second pin respectively, and a biasing member engageable with the collar to fix the first pin and the second pin in the locked orientation.

17. A spinal implant system comprising:
- a spinal implant including a first member defining a longitudinal axis, and including a rod, an arcuate portion and a plurality of transverse grooves, a second member including a rod, an arcuate sleeve and a surface defining at least one longitudinal slot, and a ratchet disposed with the members including the at least one longitudinal slot and the plurality of transverse grooves;
- a first bone fastener; and
- a second bone fastener,
- the rod of the first member being configured for fixation with a posterior surface of a first vertebra via the first bone fastener and the rod of the second member being configured for fixation with a posterior surface of a second vertebra via the second bone fastener such that the second vertebra is disposed at a first angle relative to the first vertebra in a sagittal plane of the vertebrae,
- the first member being incrementally movable relative to the second member from the first angle to a selected angle of the second vertebra relative to the first vertebra in the sagittal plane,
- in an expandable orientation a first pin is disposed in the at least one longitudinal slot to allow expansion of the first member in a first direction relative to the second member, and
- in a locked orientation the first pin is longitudinally biased into locking engagement with the surface and one of the plurality of transverse grooves to prevent movement of the first member relative to the second member in a second opposite direction.

18. A spinal implant system as recited in claim 17, wherein the second member includes a sleeve and the at least one longitudinal slot includes a tapered slot configured for disposal of the first pin, and the first member includes a rod including the plurality of transverse grooves such that the sleeve and the rod are incrementally expandable.

19. A spinal implant system as recited in claim 17, wherein the second member includes a surface defining a second longitudinal slot configured for disposal of a second pin.

20. A spinal implant system as recited in claim 17, wherein the at least one longitudinal slot includes a tapered slot such that the locking engagement includes the first pin being wedge fit with the surface and the transverse groove.

* * * * *